United States Patent
Linker et al.

(10) Patent No.: US 6,572,825 B1
(45) Date of Patent: Jun. 3, 2003

(54) APPARATUS FOR THERMALLY EVOLVING CHEMICAL ANALYTES FROM A REMOVABLE SUBSTRATE

(75) Inventors: Kevin L. Linker, Albuquerque, NM (US); David W. Hannum, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/410,976

(22) Filed: Oct. 4, 1999

(51) Int. Cl.[7] ................................................ G01N 27/30
(52) U.S. Cl. ................. 422/82.01; 422/82.03; 422/98; 422/60; 422/80
(58) Field of Search ................ 436/153, 106; 422/98, 82.01, 82.03, 60, 80

(56) References Cited

U.S. PATENT DOCUMENTS

| | | | |
|---|---|---|---|
| 4,013,532 A | * | 3/1977 | Cormia et al. ............... 204/164 |
| 5,436,129 A | * | 7/1995 | Stapleton .................... 204/450 |
| 5,532,128 A | * | 7/1996 | Eggers et al. .................. 435/16 |
| 5,653,939 A | * | 8/1997 | Hollis et al. ................... 422/50 |
| 5,728,532 A | * | 3/1998 | Ackley ........................... 435/6 |
| 5,874,314 A | * | 2/1999 | Loepfe et al. ............... 436/111 |
| 6,120,662 A | * | 9/2000 | Edwards et al. ............. 204/400 |
| 6,238,909 B1 | * | 5/2001 | Choong et al. ........... 435/287.2 |

* cited by examiner

*Primary Examiner*—Jill Warden
*Assistant Examiner*—Latoya Cross
(74) *Attorney, Agent, or Firm*—Russell D. Elliott; George H. Libman

(57) ABSTRACT

Method and apparatus suited to convenient field use for heating a porous metallic substrate swiped on the surface of an article possibly bearing residue of contraband or other target chemical substances. The preferred embodiment of the device includes means for holding the swiped substrate between electrodes bearing opposite electrical charges, thereby completing an electrical circuit in which current can flow through the porous metallic substrate. Resistance causes the substrate to heat, thus driving adherent target chemicals, if present, into a space from which they are carried via gas flow into a detector such as a portable IMS for analysis.

4 Claims, 3 Drawing Sheets

APPARATUS FOR THERMALLY EVOLVING CHEMICAL ANALYTES FROM A REMOVABLE SUBSTRATE

This invention was made with Government support under Contract DE-AC04-94AL85000 awarded by the U. S. Department of Energy. The Government has certain rights in the invention.

BACKGROUND OF THE INVENTION

1. Field of the Invention

This invention relates to the field of particle concentrators, and more particularly to an apparatus and method for capturing target chemical substances adherent to a substrate that has been rubbed on the surface of a test subject to test for the presence of the target chemical substances. Preconcentration of the target substances results from the rubbing (alternatively referred to herein as "swiping") of the substrate on the test surface. Specifically, according to the invention, target substances thus preconcentrated are removed (or, as the term is used herein, "evolved") from the substrate by heating the substrate in the presence of suction or other gas flow associated with a chemical analyzer such as a portable ion mobility spectrometer. Heating is accomplished by passing current through the swiped substrate, which comprises metallic felt or another similar porous metallic material. For purposes of this disclosure, including the appended claims, "suction" in association with the chemical analyzer is intended to include all modalities through which gases are caused to pass from outside of the anayzer to inside the analyzer, regardless of whether the fan or other means for causing the flow of gases into the analyzer resides inside the analyzer or external to it. The apparatus of the invention is suited to human portability and is especially useful in conjunction with detecting compounds such as explosives, illegal drugs, other controlled substances and chemical agents. For purposes of this application, in the context of describing the claimed invention, the term particle is intended not to exclude vapor.

2. Description of the Related Art

Additional background information, supplemental to the information provided here, is found in U.S. Pat. No. 5,854,431 "Particle Preconcentrator" and in pending U.S. patent application Ser. No. 09/339,349, both of which are incorporated by reference herein in their entirety.

The detection of explosives, narcotics or other chemicals is a growing part of contraband detection. Recent years have seen rapid development of detectors capable of identifying the presence of explosives by capturing and identifying either vapors emanating from explosive materials or particles of explosive material, or both. Similarly, such detectors can also identify vapors and particles associated with other forms of contraband such as illegal drugs and other controlled substances. Such vapors and particles associated with contraband may be present and detectable on or near persons or objects that have been exposed to contraband materials and substances. Suitable detectors for this purpose include, but are not limited to, ion mobility spectrometers (IMS), electron capture detectors, mass spectrometers (MS), and chemiluminescence-based systems.

Detection of explosives, narcotics or other contraband substances demands reliable and convenient means for collecting and analyzing sample. The '431 patent and the pending application Ser. No. 09/339,349 mentioned above are examples of ways to collect trace amounts of target chemical in dilute concentration in gases. The present invention offers an alternative that relates to the use of the technique of rubbing or swiping a surface of an article being tested for the presence of target chemicals.

Swiping surfaces in order to concentrate sample is well known in the art of chemical detection. A challenge remains, though, in how to reliably analyze chemicals collected and concentrated using the swiping approach, especially so that analysis results can be obtained quickly in a field setting. The present invention offers a quick and reliable method and apparatus to capture the target chemicals collected using the swiping technique and to deliver those chemicals to an analyzer for detection. An important aspect of the invention is that heat is used in a controlled fashion to drive off chemicals adherent to the swiped substrate. For purposes of this disclosure, the term "evolve" is used in conjunction with the process whereby target chemicals are driven off of the substrate as a consequence of application of heat.

SUMMARY OF THE INVENTION

The method and apparatus of the present invention rely on the use of a porous metallic substrate as the material used for swiping test surfaces. This porous metallic substrate forms part of an electrical circuit though which current passes causing the substrate to heat up. As the substrate heats in this fashion, target chemicals evolve from the surface of the substrate in a controlled manner. The evolved chemicals are then carried directly into an analyzer such as an IMS. (Other suitable analyzers include, but are not limited to, electron capture detectors, mass spectrometers and chemiluminescence-based systems.)

The apparatus of the present invention includes a heating device that can be conveniently attached to the gas inlet of an IMS or other portable detector. In the preferred embodiment, the swiped metallic substrate is held in place over an aperture opening toward the gas inlet of a portable IMS. Each end of the substrate is secured between electrode surfaces of like charge so that one end of the substrate is clamped between two positive electrodes and the other end is clamped between two negative electrodes, with the portion of the substrate between the ends positioned over the aperture. When positive and negative charges are applied to the positive and negative electrodes, respectively, current passes through the substrate, causing it to heat due to electrical resistance. At the same time, a suction capability, such as a pump, in the IMS in activated. As target chemicals evolve from the surface of the swiped substrate, they are captured and carried into the IMS for detection.

The invention includes features such as a hinged box within which the electrical elements of the apparatus are housed for convenient positioning of the substrate. In the preferred embodiment, a hinged box is used so that in an open position the substrate can be easily inserted or removed, and in the closed position the substrate is secured in place by the pairs of electrodes described.

An object of the invention is to provide an apparatus for use in collecting chemical substances from a substantially planar porous metallic substrate.

Another object of the invention is to provide a method for collecting chemical substances adhering to a substantially planar porous metallic substrate.

Yet another object of the invention is to provide an apparatus comprising a first support member including an aperture, and affixed to the first support member, in a first position adjacent to the aperture, a first electrical contact adapted to receive electrical current so that the first electrical contact can attain a positive electrical charge, and affixed to the first support member, in a second position adjacent to the aperture different from the first position, a second electrical contact adapted to receive electrical current so that the second electrical contact can attain a negative electrical charge.

Yet another object of the invention is to provide an apparatus further comprising a second support member, and affixed to the second support member, a third electrical contact adapted to receive electrical current so that the third electrical contact can attain a positive electrical charge, and a fourth electrical contact adapted to receive electrical current so that the fourth electrical contact can attain a negative electrical charge, the third and fourth electrical contacts being positioned so that when the second support member is placed adjacent to the first support member, the first electrical contact can lie substantially adjacent to the third electrical contact, and the second electrical contact can lie substantially adjacent to the fourth electrical contact.

Yet another object of the invention is to provide an apparatus whereby when a substantially planar porous metallic substrate is placed across the aperture described above. The substrate can be held at one locus on the substrate between the first and third electrical contacts, and also at a different locus on the substrate between the second and fourth electrical contacts, thereby completing an electrical circuit wherein electrical current can pass through the substrate.

Another object of the invention is to provide a method for collecting target chemical substances comprising the steps of rubbing a substantially planar porous metallic substrate on an article to which at least one target chemical substance adheres, positioning the substrate so that a portion of the substrate lies across an aperture connected to a chemical analyzer including a suction capability, forming electrical contact between a first electrode and a first locus of the substantially planar porous metallic substrate, forming electrical contact between a second electrode and a second locus of the substantially planar porous metallic substrate, the second locus being different from the first locus, whereby when electrical potentials of opposite charge are applied to the first and second electrodes current can flow through the substrate between the first locus and the second locus, applying potentials of opposite charge to the first and second electrodes of sufficient magnitude to cause current to pass through the substrate and heat the substrate so that at least portion of the at least one target chemical substance evolves from the substrate, and activating the suction capability of the analyzer so that target chemical substance evolved from the substrate passes in to the analyzer and subjected to chemical analysis.

An advantage of the present invention is that it provides a convenient and reliable method and apparatus for collecting target chemicals adherent to a swiped substrate and delivering those target chemicals to a detector for analysis.

Other objects, advantages and novel features will become apparent to those skilled in the art upon examination of the following description or may be learned by practice of the invention. The objects and advantages of the invention may be realized and attained by means of the instrumentalities and combinations particularly pointed out in the appended claims.

DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

The present invention represents an improvement over earlier art in the area of target chemical substance collection and preconcentration. The invention provides for convenient removal, capture and analysis of chemical substances adherent to a substrate swiped on one or more test surfaces. It is suited to field applications, and specifically, hand held or otherwise human portable use, since it employs a simple, lightweight heating device that easily adapts to existing hand-held portable detection machines such as a portable IMS. It is also suited to use with DC power sources well known in the field of portable electronic systems.

Fundamentally, the invention uses electrical current passed through a porous metallic substrate on which target chemical substances may be present, to cause those substances to evolve from the substrate into a region of controlled gas flow. Substances caused to evolve in this way are easily carried directly to a detector.

Figure 1:
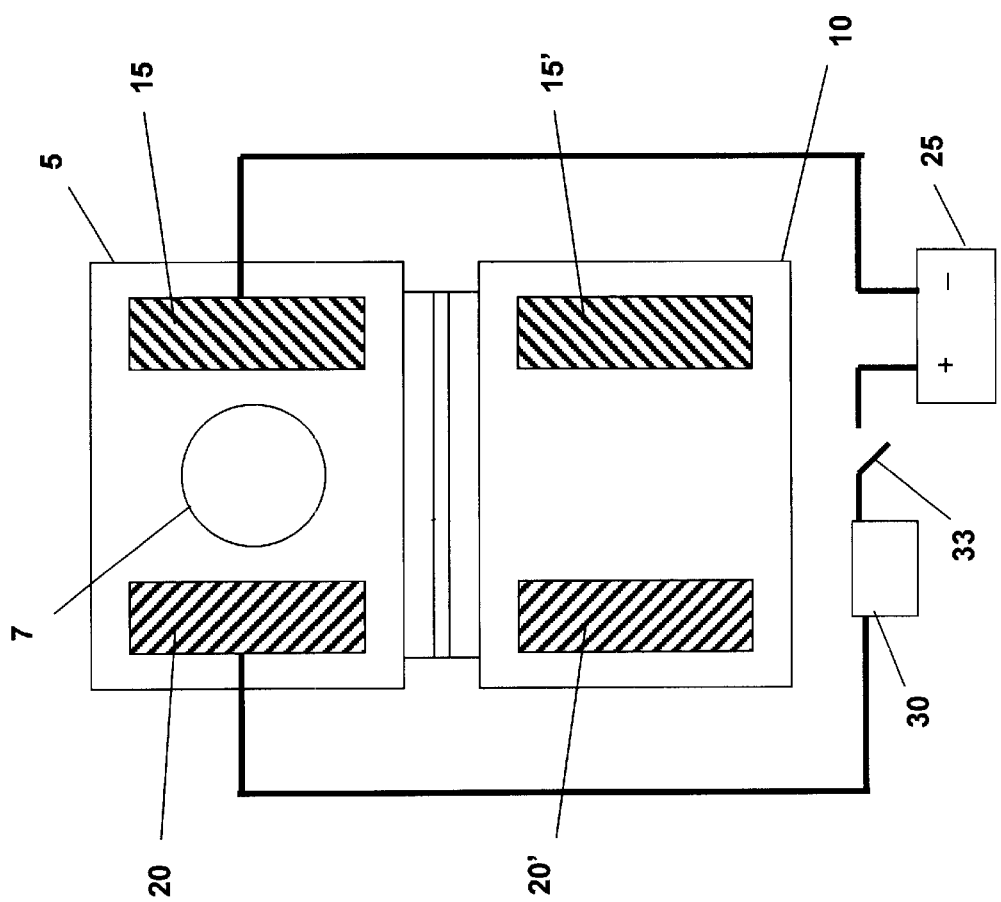
FIG. 1 is a schematic diagram showing some of the electrical features of the invention

Referring to FIG. 1, two panels 5 and 10 are shown. The first panel 5 includes an aperture 7 located generally in the central region of the panel. The second panel 10 need not have a similar aperture. Each panel also has two electrode surfaces affixed to it. In the preferred embodiment, the electrode surfaces on the first panel 5 are positioned generally on opposite sides of the aperture 7. The electrodes on the first panel, when the apparatus is in operation, exhibit opposite electrical charges. For convenience, in this disclosure the first electrode 15 is designated the negative electrode and the second electrode 20 is designated the positive electrode. It should be recognized that the invention requires only that, in operation, these two electrodes have opposite charges, and it does not matter which of the two is negatively charged and which is positively charged. As a convention in this disclosure, however, for clarity the designations noted for positive and negative will be maintained.

The electrodes on the second panel, likewise are designated, for convenience, as negative 15' and positive 20'. The electrodes on the second panel are positioned similarly to those on the first panel. Specifically the electrodes are positioned so that when the two panels 5 and 10 are placed facing each other with the electrodes opposing, the positive electrode 20 on the first panel 5 and the positive electrode 20' on the second panel 10 align substantially with one another, and the negative electrode 15 on the first panel 5 and the negative electrode 15' on the second panel 10 are likewise in substantial alignment.

Also shown in FIG. 1 are a DC power supply 25, a heating control 30 and a switch 33 for activating the circuit. In the preferred embodiment, the switch 33 is a safety switch that is activated when the first and second panels, 5, 10 are in the closed position, facing each other. (The switch can be located anywhere in the circuit where it will perform its designated switching function to activate or deactivate the circuit. The location of the switch 33 in the circuit need not necessarily be between the heating control 30 and the power supply 25.) Finally, black lines are shown in the figure illustrating that the negative electrode 15 is electrically connected to the negative pole of the DC power supply 25 and the positive electrode 20 is electrically connected to the positive pole of the DC power supply 25. In the figure, the heating control 30 (which can be a rheostat, switch or other electrical component suited to current flow control) is shown as being positioned in the circuit between the positive pole of the power supply and the positive electrodes. (The heating control 30, however could equally well be placed in the circuit between the negative pole of the power supply and the negative electrodes.) All that remains for current to flow in the circuit illustrated in FIG. 1 is an electrical connection between the negative and positive electrodes 15, 15' and 20, 20'. This connection is provided by the porous metallic substrate, as illustrated in FIG. 2A and FIG. 2B.

Figure 2B:
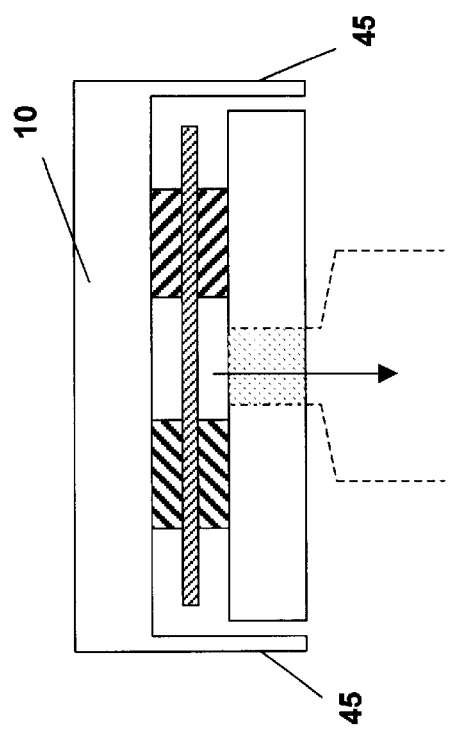
FIGS. 2A and 2B are schematic cross-section diagrams showing from the top view how the swiped substrate is secured between electrodes during evolution of target chemicals
Figure 2A:
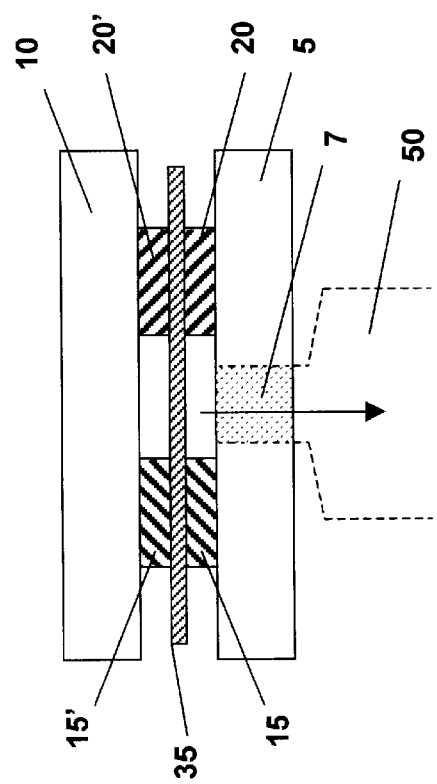

Referring to FIG. 2A, a top view cross-section is depicted of the first and second panels positioned opposing one another, with a swiped substrate positioned between the electrodes in an operative configuration. (As described before, the swiped substrate would be rubbed on a test surface to collect target chemicals if present prior to being placed in the apparatus.) As the Figure illustrates, the swiped porous metallic substrate 35 is held in position on one end between the negative electrodes 15 and 15', and on the other end between the positive electrodes 20 and 20'. A portion of the swiped substrate is exposed to the aperture 7 of the first panel 5. When current is passed through the substrate as a result of opposite charges being applied to the electrode pairs, adherent chemicals residing on the surface of the substrate in the region near the aperture evolve. These are drawn into a detector 50 (as a result of a suction means in the detector, for example) along with gases flowing in the direction of the arrow shown in the Figure. The detector then analyzes the substances that were picked up on the substrate when it was swiped on a test surface.

It is possible to include features in the panels, for example, to optimize the flow of air and other gases through the porous substrate 35 and into the detector 50. It has been observed by the inventors, though, that favorable results are obtained in field-type applications, even without special air flow configurations beyond what has been described here. There is enough leakage around the various components that gases flow easily through the substrate, via the aperture, into the detector, resulting in favorable detection results.

FIG. 2B illustrates a slight variation wherein the second panel 10 has extensions 45 similar to the sides of a box. This may be beneficial for certain applications since using a box-style configuration provides a slightly better enclosure with limited leakage versus the configuration in FIG. 2A. The functions of the two configurations, however, are nearly identical.

Figure 3:
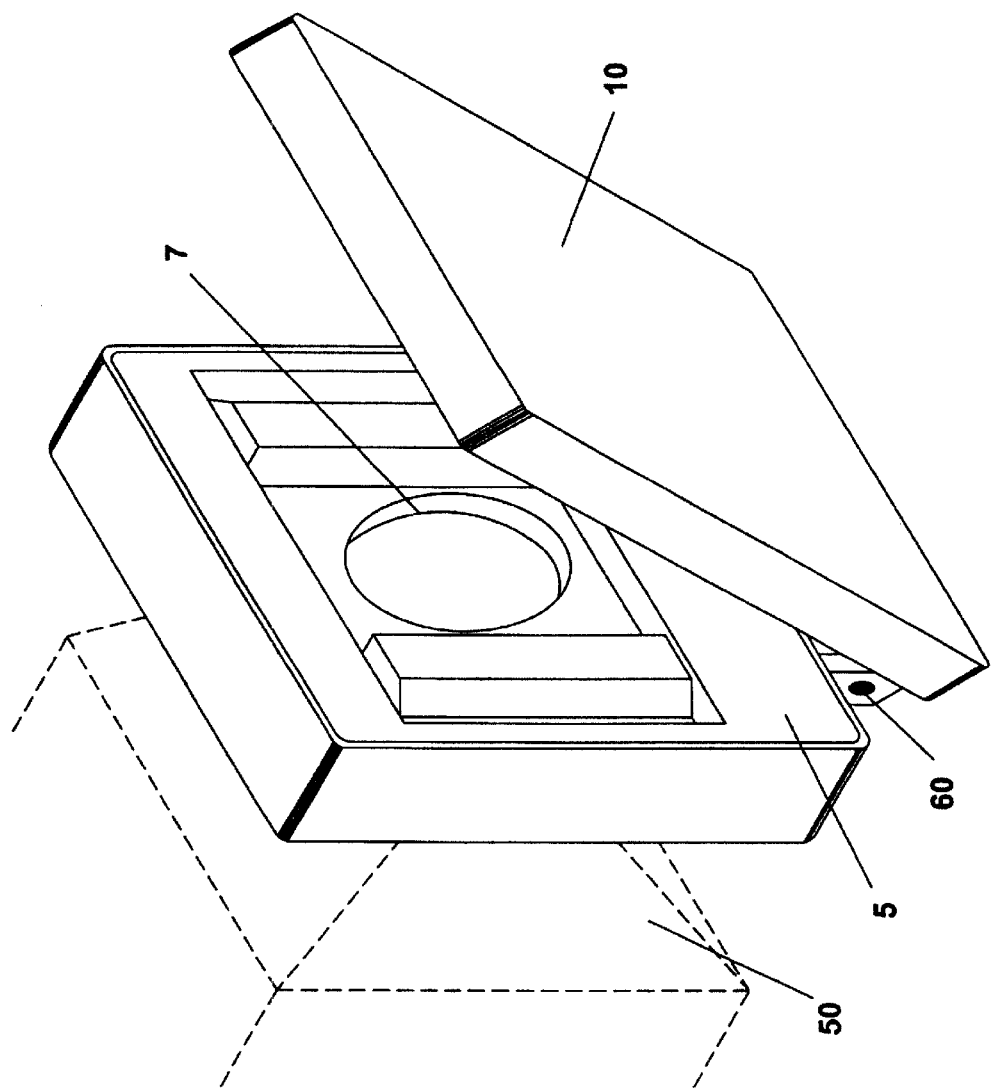
FIG. 3 is a perspective view of a preferred embodiment of the apparatus of the present invention.

FIG. 3 illustrates the preferred embodiment of the present invention apparatus wherein the first panel 5 is shown attached to a detector 50, with the aperture 7 connected to the gas inlet of the detector. The second panel 10 is attached to the first panel 5 by means of a hinge 60 running along adjacent edges of the first and second panels 5 and 10. The hinge 60 is adapted so that the second panel 10 can conveniently move apart from the first panel 5 with the apparatus in a "open" position. When in this position, a substrate can be placed in the apparatus for testing or removed afterwards. Alternatively, when in the closed position, a substrate placed in the apparatus completes the electrical circuit and can be heated as described in this disclosure.

The invention method and apparatus require that the substrate be heated sufficiently to cause target chemicals to evolve, but not so much as to unnecessarily degrade the substrate. It is believed that for most target chemicals, the substrate can be heated sufficiently to drive off all target analyte, leaving the substrate clean for future use. For target chemicals such as TNT, RDX and various narcotic substances, the inventors have experienced success in detection by heating the substrate to within the range of 100 C to. 200 C, with the best results occurring between 150 C. and 200 C. The optimal temperature, however, for causing chemicals to evolve from the substrate will depend on the target chemicals, themselves.

It is intended that the scope of the invention be defined by the claims appended hereto. Although the invention has been described in detail with particular reference to preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

We claim:

1. An apparatus for use in evolving chemical substances from a substantially planar porous metallic substrate upon which the substances have been collected, the apparatus comprising:

a substantially porous metal substrate for collecting chemical substances;

a first support member made of electrically insulating material and including an aperture through said support member for the passage of evolved substances, a first electrical contact affixed to the first support member, in a first position, a second electrical contact affixed to the first support member in a second position opposite the aperture from the first position, each of said first and second electrical contacts having an outer surface spaced from said first support member, a second support member made of electrically insulating material, and a hinge connecting the first and second support members to permit the second support member to move relative to the first support member in rotation about the hinge from an open position wherein said support members are adjacent only at said hinge to a closed position wherein the outer surface of said contacts face said second support member, whereby in the open position said substrate can be removed from said support members and when said substrate is between the support members in the closed position, said substrate touches the first and second electrical contacts, thereby completing an electrical circuit wherein electrical current can pass through the substrate to evolve chemical substances through the aperture.

2. The apparatus of claim 1 further comprising a second pair of spaced electrical contacts affixed to the second support member such that when said support members are holding a substrate in the closed position, each of said first and second electrical contacts on said first support member is aligned with one of said second pair of electrical contacts on said second support member, all of said electrical contacts pressing against said substrate.

3. An apparatus for use in collecting chemical substances, the apparatus comprising:

a substantially planar porous metallic substrate for collecting chemical substances;

a first support member including an aperture extending through said support member and adapted to communicate with a chemical analyzer including a suction capability, affixed to the first support member, in a first position adjacent to the aperture, a first electrical contact adapted to receive electrical current so that the first electrical contact can attain a positive electrical charge, affixed to the first support member, in a second position adjacent to the aperture different from the first position, a second electrical contact adapted to receive electrical current so that the second electrical contact can attain a negative electrical charge, a second support member, affixed to the second support member, a third electrical contact adapted to receive electrical current so that the third electrical contact can attain a positive electrical charge, and a fourth electrical contact adapted to receive electrical current so that the fourth electrical contact can again a negative electrical charge, the third and fourth electrical contacts being positioned so that when the second support member is placed adjacent to the first support member, the first electrical contact can lie substantially adjacent to the third electrical contact, and the second electrical contact can lie substantially adjacent to the fourth electrical contact, and a hinge connected to the first and second support members, the hinge being adapted to permit the second support member to move relative to the first support member in rotation about the hinge, whereby when said substantially planar porous metallic substrate is placed across the aperture, the substrate can be held at one locus on the substrate between the first and third electrical contacts, and also at a different locus on the substrate between the second and fourth electrical contacts, thereby completing an electrical circuit wherein electrical current can pass through the substrate.

4. The apparatus of claim 3, wherein the first and second electrical contacts are positioned on opposite sides of the aperture.

* * * * *